United States Patent [19]
Pomeranz et al.

[11] Patent Number: 5,558,073
[45] Date of Patent: *Sep. 24, 1996

[54] ENDOCARDIAL MAPPING APPARATUS WITH ROTATABLE ARM AND METHOD

[75] Inventors: Mark L. Pomeranz, Los Gatos, Calif.; Patsy A. Gingell, Pascoag, R.I.; Mir A. Imran, Palo Alto, Calif.

[73] Assignee: Cardiac Pathways Corporation, Sunnyvale, Calif.

[ * ] Notice: The term of this patent shall not extend beyond the expiration date of Pat. No. 5,400,783.

[21] Appl. No.: 410,716

[22] Filed: Mar. 27, 1995

Related U.S. Application Data

[63] Continuation of Ser. No. 135,048, Oct. 12, 1993, Pat. No. 5,400,783.

[51] Int. Cl.⁶ .......................... A61B 5/0408; A61N 1/05
[52] U.S. Cl. ............... 128/642; 607/122; 606/41
[58] Field of Search .................... 128/642; 607/122, 607/125, 126; 606/41

[56] References Cited

U.S. PATENT DOCUMENTS

| | | | |
|---|---|---|---|
| 4,522,212 | 6/1985 | Gelinas et al. | 128/642 |
| 4,699,147 | 10/1987 | Chilson et al. | 128/642 |
| 5,156,151 | 10/1992 | Imran | 128/642 |
| 5,237,996 | 8/1993 | Waldman et al. | 128/642 |
| 5,255,679 | 10/1993 | Imran | 128/642 |
| 5,263,493 | 11/1993 | Avitall | 128/642 |
| 5,293,869 | 3/1994 | Edwards et al. | 128/642 |
| 5,324,284 | 6/1994 | Imran | 607/122 |
| 5,400,783 | 3/1995 | Pomeranz et al. | 128/642 |

*Primary Examiner*—Lee S. Cohen
*Attorney, Agent, or Firm*—Flehr, Hohbach, Test, Albritton & Herbert

[57] ABSTRACT

An endocardial mapping apparatus for mapping the wall of a chamber of the heart having blood therein. The apparatus includes a flexible elongate tubular member having proximal and distal extremities and at least one lumen extending therethrough. A basket assembly is carried by the distal extremity of the flexible elongate tubular member and is movable between contracted and expanded positions. The basket assembly has a plurality of elongate flexible circumferentially spaced-apart arms with joined proximal and distal extremities and a plurality of longitudinally spaced-apart electrodes carried by each arm for engaging the wall of the heart. The arms have spaces therebetween when the basket assembly is in an expanded position. An elongate flexible rotatable member is rotatably coupled to the joined distal extremities and is disposed within the basket assembly. At least one electrode is carried by the rotatable member for engaging the wall of the heart. A torque knob is coupled to the rotatable member for rotating the member within the basket assembly and for bowing it radially outwardly into a space between the arms so as to engage the wall of the heart along a portion of the length thereof for mapping and/or ablating.

9 Claims, 1 Drawing Sheet

U.S. Patent  Sep. 24, 1996  5,558,073
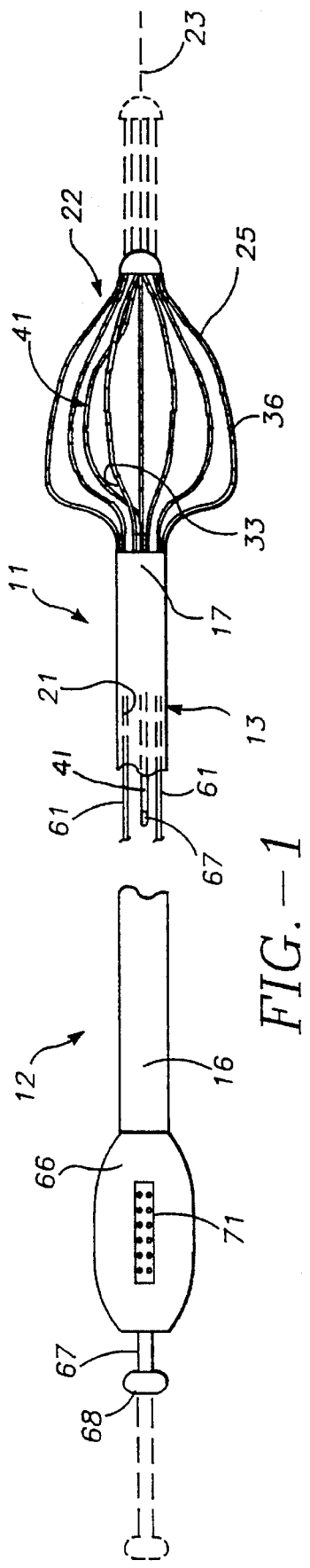
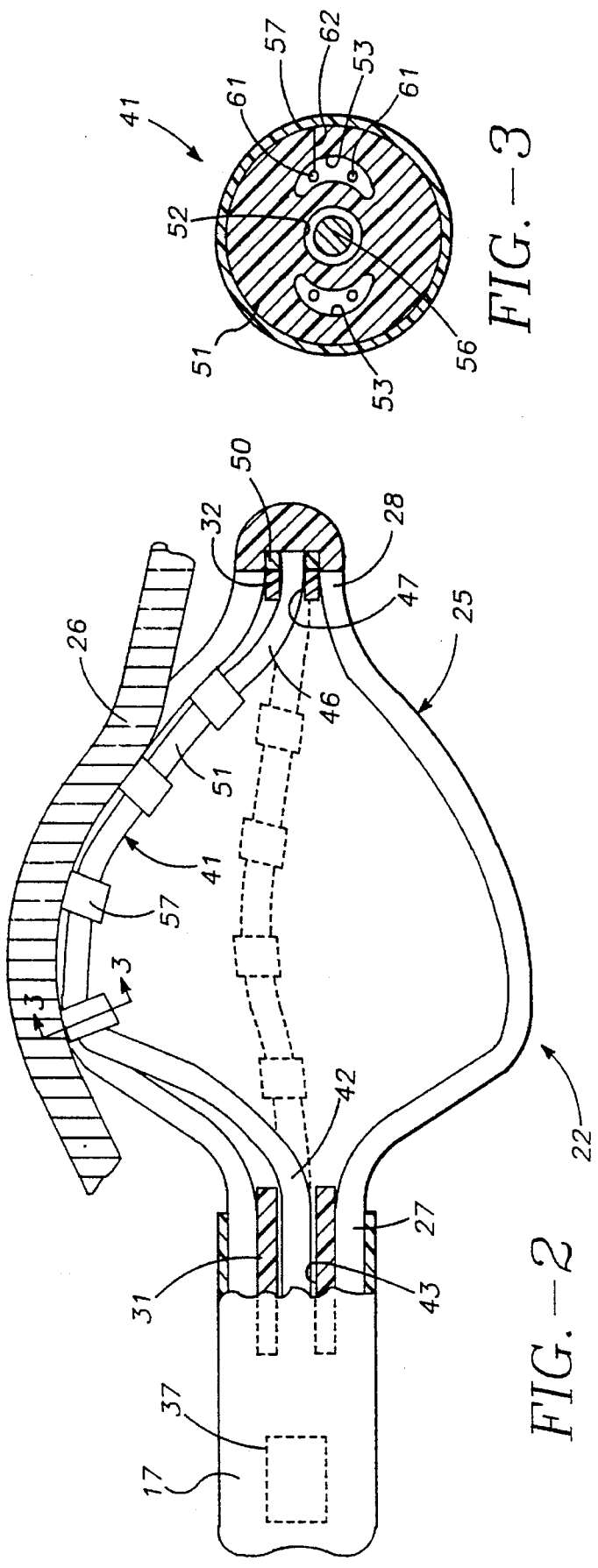

ENDOCARDIAL MAPPING APPARATUS WITH ROTATABLE ARM AND METHOD

This is a continuation of application Ser. No. 08/135,048 filed Oct. 12, 1993, now U.S. Pat. No. 5,400,783.

BACKGROUND OF THE INVENTION

1. Field of the Invention

This invention pertains generally to medical apparatus for performing endocardial mapping and, more specifically, to endocardial mapping apparatus having a basket assembly with an array of electrodes thereon.

2. Description of the Related Art

Catheters have been provided with basket assemblies on the distal end for performing endocardial mapping. These basket assemblies are formed from a plurality of elongate flexible circumferentially-spaced arms which substantially engage the endocardium and permit blood in the heart to flow therethrough. The arms have a plurality of longitudinally-spaced electrodes thereon which are electrically connected to a multiplexer chip. In some of these basket assemblies, for example the basket assemblies of applications Ser. No. 08/044,255 filed Apr. 7, 1993, U.S. Pat. No. 5,327,889 filed Dec. 1, 1992 and U.S. Pat. No. 5,156,151 filed Feb. 15, 1991, the spacing between the arms is larger than would be desired for mapping purposes. In addition, there have been difficulties in effectively ablating with the small low mass electrodes of these arms. Performing ablations with the mapping electrodes also enhances the complication of the multiplexer chip. Because of the foregoing, there is a need for a new and improved endocardial mapping apparatus which overcomes the above named disadvantages.

OBJECTS OF THE INVENTION

In general, it is an object of the present invention to provide an endocardial mapping apparatus having a basket assembly with a plurality of expandable arms for engaging the wall of the heart and having a rotatable arm which can sense electrical impulses between the arms of the basket assembly.

Another object of the invention is to provide a mapping apparatus with a rotatable arm of the above character which can perform ablations in the spaces between the arms of the basket assembly.

Additional objects and features of the invention will appear from the following description from which the preferred embodiments are set forth in detail in conjunction with the accompanying drawings.

BRIEF DESCRIPTION OF THE DRAWINGS

FIG. 1 is a side elevational view of an endocardial mapping apparatus with rotatable arm of the present invention.

FIG. 2 is an enlarged view, partially sectioned and somewhat schematic of the distal extremity of the endocardial mapping apparatus of FIG. 1 partially engaging a portion of the wall of the heart.

FIG. 3 is a cross-sectional view taken along the line 3—3 of FIG. 2.

SUMMARY OF THE INVENTION

In general, the endocardial mapping apparatus of the present invention is for mapping the wall of a chamber of the heart having blood therein. The apparatus includes a flexible elongate tubular member having proximal and distal extremities and at least one lumen extending therethrough. A basket assembly is carried by the distal extremity of the flexible elongate tubular member and is movable between contracted and expanded positions. The basket assembly has a plurality of elongate flexible circumferentially spaced-apart arms with joined proximal and distal extremities and a plurality of longitudinally spaced-apart electrodes carried by each arm for engaging the wall of the heart. The arms have spaces therebetween when the basket assembly is in an expanded position. An elongate flexible rotatable member is rotatably coupled to the joined distal extremities and is disposed within the basket assembly. At least one electrode is carried by the rotatable member for engaging the wall of the heart. Means is coupled to the rotatable member for rotating the member within the basket assembly and for bowing it radially outwardly into a space between the arms so as to engage the wall of the heart along a portion of the length thereof for mapping and/or ablating.

DETAILED DESCRIPTION

More particularly, apparatus 11 of the present invention is for mapping the wall of a chamber of the heart having blood therein and includes a catheter probe 12 described in detail in copending application Ser. No. 08/044,255 filed Apr. 7, 1993. Briefly, catheter probe 12 includes a flexible elongate tubular member or shaft 13 formed of a suitable material such as plastic which is circular in cross section and has proximal and distal extremities 16 and 17 (See FIG. 1). Shaft 13 is provided with at least one lumen 21, which is circular in cross section and extends therethrough from proximal extremity 16 to distal extremity 17, and carries a basket assembly 22 at its distal extremity. Basket assembly 22 has a central longitudinal axis 23 and is moveable between contracted and expanded positions substantially therealong as shown, respectively, by the dotted and solid lines in FIG. 1.

Basket assembly 22 is provided with a plurality of longitudinally extending flexible arms 25 which have an outwardly bowed shaped memory for expanding the basket assembly into engagement with wall 26 of the heart as shown in FIG. 2. Arms 25 have proximal extremities or end portions 27 which are mounted circumferentially about a tubular member or mandrel 31 connected to distal extremity 17 of shaft 13 so as to be joined and distal extremities or end portions 28 which are similarly joined by a ring 32 at tip 35 of basket assembly 22. Both mandrel 31 and ring 32 are made of any suitable material such as polyethylene or TEFLON. When expanded, arms 25 are circumferentially and symmetrically spaced-apart and have a plurality of spaces or openings 33 therebetween. A plurality of longitudinally spaced-apart electrodes 36 are carried by each arm 31 for engaging heart wall 26 and are electrically coupled to a multiplexer chip 37 for transmitting electrical signals sensed thereby to shaft proximal extremity 16. The arms can also carry a plurality of longitudinally spaced-apart radiopaque markers or traces, not shown in the drawings, formed of a suitable material such as platinum or gold to permit fluoroscopic viewing of the basket assembly.

An elongate flexible rotatable member or arm 41 is carried by shaft distal extremity 17 and by distal end portion 28 of basket assembly 22 and can be bowed outwardly from a first position within basket assembly 22, as shown in dotted lines in FIG. 2, to a second position in engagement with heart wall 26, as shown in solid lines in FIG. 2. Arm 41 is circular in cross section and has a proximal end portion 42 which rotatably and slidably extends through lumen 21 of the shaft and a bore 43 formed longitudinally through the center of mandrel 31. Arm 41 has a distal end portion 46 which rotatably extends through a bore 47 provided in the center of ring 32 and has a retaining ring 50 crimped on the end thereof for rotatably coupling and connecting arm 41 to ring 32. The inner surfaces forming bores 43 and 47 are circular in cross section and serve as bearing surfaces to facilitate the relative smooth movement of rotatable arm 41 in mandrel 31 and ring 32.

Rotatable arm 41 has a tube 51 formed of a suitable material such as plastic and provided with a longitudinally extending central bore 52 which is circular in cross section and two crescent shaped outer bores 53 circumferentially disposed about central bore 52 (See FIG. 3). A core element or wire 56 made of any suitable superelastic material extends through central bore 52 to provide rotatable arm 41 with an outwardly bowed shaped memory. Tube 51 has an outer diameter ranging from 0.040 to 0.070 inch and wire 56 has a diameter ranging from 0.010 to 0.025 inch. Mandrel 31 and ring 32 can have a longitudinal dimension on the order of 0.125 to 0.500 inch.

At least one electrode 57, and as shown four longitudinally spaced-apart electrodes 57, are carried by rotatable arm 41 for engaging heart wall 26. Electrodes 57 are made of any suitable material such as platinum and are generally tubular in shape, being snugly disposed about the circumference of tube 51. A plurality of lead means in the form of conductors 61 are disposed within outer bores 53 and are electrically connected at one end to respective electrodes 57 by electrical connectors 62 extending through tube 51 as illustrated in FIG. 3. Conductors 61 extend longitudinally through shaft 13 to proximal extremity 16 thereof. It should be appreciated, however, that conductors 61 could be coupled to multiplexer chip 37 and be within the scope of the present invention.

Electrodes have a significant mass in comparison to electrodes 36 of basket assembly 22 and, in this regard, have a length on the order of one to three millimeters, an outer diameter on the order of 0.040 to 0.075 inch and a thickness of approximately 0.003 inch. It should be appreciated that rotatable arm 41 and electrodes 57 thereon can be cooled in the manner disclosed in U.S. Pat. No. 5,348,554 filed Dec. 1, 1992 and be within the scope of the present invention. The rotatable arm can also be provided with radiopaque markers or traces of the type and for the purpose discussed above.

A handle 66 is carried by proximal extremity 16 of shaft 13 for operating apparatus 11. A torque cable 67 is joined to proximal end portion 42 of rotatable arm 41 and extends through lumen 21 of shaft 13 and out the end of the handle so as to be accessible by the operating physician. A torque knob 68 is fixed to the accessible end of the torque cable and is included within the means of apparatus 11 for rotating and swinging arm 41 within basket assembly 22 and for bowing arm 41 radially outwardly into an opening 33 between arms 25 of the basket assembly. A connector 71 is included on handle 66 and is electrically connected to multiplexer chip 37 and electrodes 36 of the basket assembly and conductors 61 and electrodes 57 of rotatable arm 41. A power supply, a controller and a radio frequency generator can be connected to connector 71 for operating apparatus 11. In operation and use, basket assembly 22 can be introduced into a ventricle of a heart and operated in substantially the same manner as discussed in U.S. Pat. No. 5,279,299 filed Jul. 24, 1992 and U.S. Pat. No. 5,324,284 filed Jun. 5, 1992. Once positioned within the chamber of the heart, the operating physician causes basket assembly 22 to expand to a stationary position within the heart so that electrodes 36 thereof engage heart wall 26 for sensing and detecting electrical energy or impulses therefrom. Simultaneously, the shaped memory of rotatable arm 41 causes it to expand to a bowed position and to engage the heart wall so that electrodes 57 can also sense electrical energy from the heart wall.

Once the information regarding heart wall 26 obtained from electrodes 36 and/or 57 has been analyzed, the method and apparatus of the present invention permit sensing electrical impulses from heart wall 26 in an opening 33 between basket assembly arms 25 where finer resolution to the mapping is desired. In this regard, torque knob 68 is pulled outwardly from handle 66 by the operating physician to cause rotatable arm 41 to collapse within basket assembly 22. The torque knob is then rotated to swing the rotatable arm circumferentially within basket assembly 22 into registration with the appropriate opening 33. If the rotatable arm engages a protuberance within the heart so as to restrict its rotation, the torque knob can be pulled further so as to cause the rotatable arm to become more straightened and thereby avoid the protuberance. After rotatable arm 41 has been swung or rotated into registration with the desired opening 33, torque knob 67 is released slowly to permit the rotatable arm to bow outwardly again to its shaped memory configuration and engage heart wall 26 in the opening 33 along a portion of the length of the rotatable arm. The circular profile of electrodes 57 increase their ability to engage the sometimes irregular shaped heart wall for mapping. In this manner, electrodes 57 can simultaneously sense electrical impulses from heart wall 26 in an opening 33.

Radio frequency energy can also be applied to electrodes 57 for ablating heart wall 26 in the opening 33. Since electrodes 57 can be directly connected to connector 71 without having to pass through multiplexer chip 37, the chip can be simpler in design and less expensive than a multiplexer chip which can accommodate radio frequency energy for ablations. The relatively large mass of electrodes 57 reduces the rate of temperature increase and the upper temperature of electrodes 57 during ablations and thereby reduces undesirable blood coagulation which can be caused by electrodes elevated in temperature to a range of 95° to 100° C.

In view of foregoing, it can be seen that an endocardial mapping apparatus having a basket assembly with a plurality of expandable arms for engaging the wall of the heart and having a rotatable arm which can sense electrical impulses between the arms of the basket assembly has been provided. The rotatable arm can also perform ablations in the spaces between the arms of the basket assembly.

What is claimed is:

1. An apparatus for mapping and/or ablating the wall of a chamber of a heart having blood therein comprising a flexible elongate tubular member having proximal and distal extremities and at least one lumen extending therethrough, expandable means carried by the distal extremity of the flexible elongate tubular member for moving between contracted and expanded positions, the expandable means having a distal extremity and a plurality of spaced-apart electrodes for engaging the wall of the heart, the expandable means being provided with spaces between electrodes when the expandable means is in an expanded position, an elongate flexible element having a distal extremity disposed within the expandable means and coupled to the distal extremity of the expandable means, at least one electrode carried by the distal extremity of the elongate flexible element for engaging the wall of the heart and means coupled to the elongate flexible element for moving a portion of the distal extremity of said element into a space between electrodes so as to engage the wall of the heart for mapping and/or ablating.

2. The apparatus of claim 1 wherein the expandable means has a proximal extremity with a center and wherein the elongate flexible element is a rotatable member having a proximal extremity which is rotatable at said center.

3. The apparatus of claim 2 wherein the lumen extends longitudinally through said center and wherein the proximal extremity of the rotatable member is slidably disposed within the lumen so as to be movable from a first position within the expandable means to a second position in engagement with the wall of the heart.

4. An apparatus for mapping and/or ablating the wall of a chamber of a heart having blood therein comprising a flexible elongate tubular member having proximal and distal extremities and at least one lumen extending therethrough, expandable means carried by the distal extremity of the flexible elongate tubular member for moving between contracted and expanded positions, the expandable means carrying a plurality of spaced-apart electrodes for engaging the wall of the heart and being provided with spaces between electrodes when the expandable means is in an expanded position, an elongate flexible member disposed within the expandable means and being movable into registration with the spaces between electrodes, at least two longitudinally spaced-apart electrodes carried by the elongate flexible member along a portion of the length thereof for engaging the wall of the heart and means coupled to the elongate flexible member for moving the portion of the elongate flexible member into a space between electrodes of the expandable means so that the electrodes carried by the portion of the elongate flexible member engage the wall of the heart for mapping and/or ablating.

5. An apparatus as in claim 4 wherein said expandable means includes a plurality of elongate flexible circumferentially spaced-apart arms with proximal and distal extremities, a plurality of longitudinally spaced-apart electrodes carried by each arm.

6. The apparatus of claim 5 wherein the elongate flexible member has a bowed configuration when in the expandable means and wherein the means for moving the elongate flexible member includes means for swinging the bowed configuration of the elongate flexible member into a space between electrodes.

7. A method for mapping the wall of a chamber of a heart with an expandable assembly disposed in a chamber of the heart in a stationary position, the expandable assembly having a plurality of electrodes and being provided with an opening therein between electrodes, comprising the step of simultaneously sensing a plurality of electrical impulses from the wall in the opening of the expandable assembly.

8. The method of claim 7 together with the step of obtaining information regarding the heart from the electrodes of the expandable assembly.

9. The method of claim 7 together with the step of ablating the wall in a space between electrodes.

* * * * *